United States Patent
Kowarschik et al.

(10) Patent No.: US 10,223,820 B2
(45) Date of Patent: Mar. 5, 2019

(54) IMAGE PROCESSING OF FOUR-DIMENSIONAL ANGIOGRAPHY DATA SET

(71) Applicants: Markus Kowarschik, Nürnberg (DE); Sonja Gehrisch, Nürnberg (DE); Christopher Rohkohl, Brixen im Thale (AT)

(72) Inventors: Markus Kowarschik, Nürnberg (DE); Sonja Gehrisch, Nürnberg (DE); Christopher Rohkohl, Brixen im Thale (AT)

(73) Assignee: Siemens Healthcare GmbH, Erlangen (DE)

(*) Notice: Subject to any disclaimer, the term of this patent is extended or adjusted under 35 U.S.C. 154(b) by 0 days.

(21) Appl. No.: 15/874,998

(22) Filed: Jan. 19, 2018

(65) Prior Publication Data
US 2018/0218521 A1 Aug. 2, 2018

(30) Foreign Application Priority Data
Jan. 27, 2017 (DE) .......... 10 2017 201 330

(51) Int. Cl.
*G06T 11/20* (2006.01)
*A61B 6/00* (2006.01)
*G06T 11/00* (2006.01)

(52) U.S. Cl.
CPC .......... *G06T 11/206* (2013.01); *A61B 6/465* (2013.01); *A61B 6/481* (2013.01); *A61B 6/504* (2013.01);
(Continued)

(58) Field of Classification Search
None
See application file for complete search history.

(56) References Cited

U.S. PATENT DOCUMENTS

| 2014/0094680 A1 | 4/2014 | Kowarschik et al. |
| 2014/0148694 A1 | 5/2014 | Mistretta et al. |

FOREIGN PATENT DOCUMENTS

DE 102012217792 A1 4/2014

OTHER PUBLICATIONS

Davis B. et al.: "4D Digital Subtraction Angiography: Implementation and Demonstration of Feasibility", in: American Society of Neuroradiology, 2013, vol. 34, pp. 1-8, DOI:10.3174/ajnr.A3529.

(Continued)

*Primary Examiner* — Michelle Chin
(74) *Attorney, Agent, or Firm* — Lempia Summerfield Katz LLC

(57) ABSTRACT

A method is provided for image processing an angiography data set of a capture region of interest of a patient's vascular system. The method includes establishing a static time parameter set from the angiography data set, wherein the static time parameter set includes time parameters and characterizes the time profile of the contrast agent concentration for picture elements of the capture region described in the image data subsets; establishing a series of mask data sets by picture element-by-picture element application of a window function having a window width of greater than zero; selecting a subinterval in the parameter space covered by the time parameters for each instant of the series to the static time parameter set; and establishing a series of static display data sets by applying the mask data sets to a static vessel data set, which shows a vascular system perfused by the contrast agent in the capture region and which underlies or is derived from the angiography data set.

15 Claims, 3 Drawing Sheets

(52) U.S. Cl.
CPC ........ *G06T 11/008* (2013.01); *G06T 2200/24* (2013.01); *G06T 2210/41* (2013.01); *G06T 2211/404* (2013.01)

(56) References Cited

OTHER PUBLICATIONS

German Office Action for related German Application No. 10 2017 201 330.3 dated Sep. 19, 2017.

IMAGE PROCESSING OF FOUR-DIMENSIONAL ANGIOGRAPHY DATA SET

The application claims the benefit of German Patent Application No. DE 10 2017 201 330.3, filed Jan. 27, 2017, which is hereby incorporated by reference in its entirety.

TECHNICAL FIELD

The disclosure relates to a method and to a device for image processing an angiography data set of a capture region of interest of a patient's vascular system, the angiography data set including a time series of two-dimensional or three-dimensional image data subsets of the capture region which, for each spatial picture element, describe a time profile of a contrast agent concentration of a contrast agent used during capture of the angiography data set. The disclosure additionally relates to a computer program and to an electronically readable data storage medium.

BACKGROUND

The development of four-dimensional digital subtraction angiography was a major step towards reliable and readily interpretable images of a patient's vascular system in capture regions of interest. Using an X-ray device, (e.g., an X-ray device with a C-arm), with one or more rotations at different projection angles, two-dimensional projection images of the capture region of interest of the patient's vascular system are here captured while a contrast agent in the form of a contrast agent bolus moves through the vascular system in the capture region. Digital subtraction angiography projection images are obtained by subtraction of a mask image captured without contrast agent, it also being possible to perform subtraction for respective reconstructed three-dimensional image data sets. While it was known at the outset of digital subtraction angiography to produce a plurality of temporally successive three-dimensional image data sets by using digital subtraction angiography projection images captured in a specific time interval to reconstruct therefrom a three-dimensional image data subset, more recent approaches capable of yielding better image quality as well as better temporal resolution have since come into being.

One of these approaches has been described in an article by B. Davis et al., "4D Digital Subtraction Angiography: Implementation and Demonstration of Feasibility," DOI: 10.3174/ajnr.A3529. This approach proposes, initially using a large proportion of the digital subtraction angiography projection images which show the at least largely filled vessels, to reconstruct a non-time-resolved three-dimensional vessel data set which shows the entire vascular system in the capture region. The vessel data set forms the basis for continuously updating the voxel values by multiplicative embedding of the time information from the in particular normalized digital subtraction angiography projection images, such that a series of time-resolved 3D images, (e.g., of image data subsets of the four-dimensional angiography data set), is obtained. In other words, the vessel data set is ultimately used to restrict the reconstruction of the individual three-dimensional image data subsets which incorporate the temporal information from the digital subtraction angiography projection images. Multiplicative back-projection is therefore carried out. This may be understood to mean that voxels which show vessels and are located on the beam of a pixel of a projection image which shows filling with contrast agent are highlighted as filled with contrast agent at the instant of capture of the projection image.

The four-dimensional reconstruction algorithm, described in overall terms in this manner, includes a three-dimensional image reconstruction act known from digital subtraction angiography for establishing the vessel data set. Producing a high-quality vessel data set entails, as has already been described, a sufficient number of projection images which are consistently filled with contrast agent. In order to provide this, it is known, on the one hand, to use an image capture protocol which captures an expanded angular range, (e.g., conventionally >200°), and, on the other hand, a relatively long injection of contrast agent, (e.g., over about 7 seconds), the requirements regarding duration of contrast agent administration (and thus also the size of the bolus) being determined by blood circulation times in the capture zone of interest, (e.g., in the brain).

The described prerequisites for obtaining a high quality three-dimensional vessel data set as the basis for the four-dimensional angiography data set may, however, lead to overlapping flow phases. More precisely, there may be a temporal overlap between the arterial and the venous phase in four-dimensional digital subtraction angiography, which results in the limitation that the arterial and venous structures cannot be separately visualized and evaluated. In addition, film-like viewing of the time series of image data subsets creates impressions which are difficult to evaluate.

Remedying this problem by shortening the contrast agent injection time, therefore using a shorter bolus, is only possible with a severe reduction in quality. If, for example, injection times in the range of 0.5 to 2 seconds as are conventional in two-dimensional digital subtraction angiography are used, arterial inflow and venous outflow may indeed be clearly differentiated, but the image quality of the three-dimensional vessel data set, which is after all used as the restriction data set for the four-dimensional angiography data set, and the quality of the four-dimensional angiography data set is thus extremely low.

In particular, in interplay with vessel overlap, flow phase overlap distinctly complicates detailed analysis of disease processes, for example, in the analysis of the vessel architecture of an arteriovenous malformation (AVM) with regard to its nidus, associated aneurisms, venous stenoses and the like.

A similar issue may also occur in "2D+t" angiography data sets, e.g., time series of two-dimensional image data subsets which show the progress of contrast agent propagation in the capture region of interest. Rendering time parameters which are descriptive of contrast behavior, in particular, the time profile of contrast agent concentration, in a manner which is intuitive, readily comprehensible and not overshadowed by other effects is in general complex.

SUMMARY AND DESCRIPTION

The object of the disclosure is therefore that of enabling a more readily comprehensible and more intuitive display of historical information present in time series of two- or three-dimensional image data subsets.

The scope of the present disclosure is defined solely by the appended claims and is not affected to any degree by the statements within this description. The present embodiments may obviate one or more of the drawbacks or limitations in the related art.

A method of the kind stated in the introduction therefore provides that a static time parameter set which characterizes a time profile of contrast agent concentration for each picture element of the capture region described in the image data subsets and in particular contains absolute time parameters is established from the angiography data set. The method also includes establishing a series of mask data sets by picture element-by-picture element application of a window function which has a window width of greater than zero. The method also includes selecting another subinterval in the parameter space covered by the time parameters for each instant of the series to the time parameter set and establishing a series of static display data sets by applying the mask data sets to a static vessel data set which completely shows a vascular system perfused by the contrast agent in the capture region and which underlies or is derived from the angiography data set.

The time series of display data sets may be correspondingly rendered on a visual display device such that a readily comprehensible, intuitive rendering of a description of the time parameter is possible. The dimensionality of the time parameter set, mask data sets, display data sets, and vessel data set, all of which are in themselves static, here corresponds to that of the image data subsets, because the present disclosure is applicable both to 2D+t and to 3D+t angiography (four-dimensional angiography). A picture element accordingly corresponds to a pixel for 2D and to a voxel for 3D. The main field of application of a four-dimensional angiography data set which contains a time series of three-dimensional image data subsets will for the most part be discussed hereinafter. The window function may be normalized to an interval between 0 and 1, such that the mask data sets may be particularly simply applied to the vessel data set using the same image value dynamic range. It should be noted that it is, of course, also conceivable to vary the perceived contrast agent strength/maximum concentration by varying the value range of the window function, in particular below 1.

In certain embodiments, time series of mask data sets and display data sets, (e.g., an instant which in particular describes the location of the window in the time parameter space is assigned to each data set of a series), are produced. For example, the assigned instant may be the center of the window and/or the start of the window. In certain examples, time-ordered subintervals may succeed one another in the series of window functions, e.g., the instants within the series correspond to increasing times. For example, the window (e.g., identically shaped for all window functions) for the window functions of different instants may be "pushed" through the time parameter space, thus at least the start and/or finish thereof, in order to establish a time series which contains display data sets corresponding to temporally successive subintervals in the time parameter space. Such developments are in particular convenient in the case of absolute time parameters of the time profile of contrast agent concentration.

A particular development provides that the time parameters which describe contrast agent arrival time or instant of maximum contrast agent concentration in the respective picture element are established. Various variants are here conceivable for specifically defining the contrast agent arrival time, also known as "Bolus Arrival Time" (BAT), in the picture element. The contrast agent arrival time may accordingly be established in the picture element as the instant at which a predetermined contrast agent concentration is exceeded and/or at which a predetermined fraction of the maximum contrast agent concentration is exceeded. In this case, the time parameter set ultimately corresponds to a static BAT data set, in which the corresponding contrast agent arrival time is assigned to each spatial picture element, in particular each voxel, e.g., the time parameter set contains times but is not itself time-dependent. Using the instant of maximum contrast agent concentration is conceivable, but less convenient in many forms of bolus.

In this development, the display data sets ultimately show time series of the contrast agent profile of a virtual bolus through the capture region, wherein the instants already used in the time series of image data subsets or at least an identical number may be used. In other words, an extremely simple manner is stated for introducing a virtual bolus, which is in particular truncated and thus avoids flow phase overlap, as a display. In particular, a phase-separated, time-resolved image series of the contrast agent bolus during its entire transit time through the vessels may be provided in the form of the display data sets by temporal reshaping, specifically computational truncation. In other words, an angiography data set may be used as the basis for calculating a new 2D+t data set or 3D+t data set as a display data set time series which corresponds to a shorter contrast agent bolus profile, such that the user may more clearly understand the vessel structure and the corresponding flow patterns. It should be noted that the window width of the window function, which ultimately describes the extent of the virtual bolus, need not necessarily be truncated relative to the actual contrast agent bolus during capture of the projection images, but may instead, if appropriate, also be lengthened, for example in the case of 2D+t angiography. In summary, the disclosure states in this development a display option which relates to a notional, computationally implemented virtual contrast agent bolus, the movement of which through the vessels may be understood by the display data sets which a new angiography data set may form.

Extremely high image quality is obtained here, because the vessel data set is directly used as the basis and the time information is taken from the image data subsets or the contrast agent profile curves (e.g., time profile of contrast agent concentration) obtained therefrom.

In the use described herein of absolute time parameters which describe the arrival of the contrast agent bolus in the picture element, the window function is ultimately a kind of weighting function which renders the computationally reshaped contrast agent bolus in order to activate picture elements in the two-dimensional or three-dimensional image area, which is achieved by the mask data sets.

One specific further development in this context provides that a window function which selects all the time parameters up to a specific time is used to display influx behavior or a window function which deselects all time parameters up to a specific time is used to display outflux behavior (e.g., outflow behavior). In this manner, it is therefore possible to establish time series of display data sets which show solely influx or solely outflow behavior, by picture elements, which are activated via a mask data set and are therefore to be displayed, for later instants in the series remaining activated or by beginning with image elements which are all activated and are deactivated over time and the outflow of the contrast agent of the virtual bolus.

It should also be noted at this point that it is in principle also conceivable to consider relative time parameters in the time parameter set, for example, to use a rise time and/or a width of the contrast agent peak in the time profile as a relative time parameter. This results in interesting new visual display options.

One convenient further development may provide that window width is adapted based on user input. In this manner, using BAT as an example of a time parameter, it is possible for a user to adapt the bolus length of a virtual bolus, for example, by visually displaying a corresponding operating element together with the display data sets which are then adapted in real time to the new window width, which ultimately also indicates the length of the subinterval. It may, in particular, also be provided that the window function is modeled on a virtual bolus profile.

In addition to window width, the window function may also include at least one further shape parameter which is in particular likewise user-adjustable. In an embodiment directed towards the simulation of a virtual bolus, the window width and optionally the further shape parameters therefore describe the shape of the virtual bolus, which may be adapted by a user, such as by superimposing appropriate operating elements, (e.g., slider controls), on a user interface via which the display data sets may also be visually displayed.

A rectangular function and/or a trapezoidal function and/or a cosine-based function may be used as the window function. A rectangular function is an extremely conventional type of window function which either activates or deactivates the individual picture elements by the mask data set. In other window function shapes, in particular, a trapezoidal function and/or a cosine-based function, it is also possible for also more than two values to occur in the mask data set, such that for example image element display intensity may be slowly "ramped up" or slowly "ramped down" in a time series of display data sets, which is particularly convenient if the intention is to model a virtual bolus.

Using a cosine-based function as the window function is particularly appropriate for such a virtual bolus. In such a cosine-based function, the only shape parameter which is present in addition to the maximum of the cosine window is a shape parameter which describes the window width as a further parameter which may be related to bolus length. Accordingly, while the window width corresponds to the length of a computationally transformed virtual contrast agent bolus, adapting the center of the window such that the flow phase describes an instant corresponds to pushing the virtual bolus through the vessel system. Because window widths greater than zero are used, it is also possible to avoid merely short illumination based on the current position of the infinitely short bolus, but instead the user is provided, despite the ultimately computationally generated virtual bolus, with the impression of a realistic, interpretable display which, however, permits a clear separation of flow phases.

A further development of the method provides that the display data sets are selectably visually displayed on a visual display apparatus by an operator by an operating element. In particular, in addition to an operating element for the presentation data set to be displayed of the series, therefore for selection of the instant in a time series, it is also possible to provide operating elements for selecting the shape parameter, in particular, the window width, of the window function, (e.g., in the form of slider controls displayed in a user interface). In the case of a virtual bolus, the length of the virtual bolus may therefore, on the one hand, be adapted and, on the other hand, the bolus may be pushed through the vessel system in the capture region by the other slider. It may therefore be provided in a further development that at least one further operating element is visually displayed for adapting window width and/or at least one further shape parameter of the window function.

It should additionally be noted at this point that it is in principle also conceivable to establish or predetermine the time parameter set independently of a previously captured angiography data set which describes time profiles of a contrast agent which has actually been administered. A model of the vascular system in the capture region may be used, which may be derived from a three-dimensional digital subtraction angiography image data set, (e.g., from the vessel data set). Flow of the contrast agent bolus through the model of the vascular system may then be simulated in order to produce the time parameter set. For example, a fixed velocity of the contrast agent bolus through the vessel system may be assumed, such that for example, based on path lengths determined along mid-lines (e.g., center lines) of the blood vessels, bolus arrival times at the corresponding positions represented in image elements may be assigned, such that a BAT data set is likewise obtained as a time parameter set. Therefore, if only a static representation of the vascular system in the capture region is available, (e.g., in the form of the vessel data set), it is here also possible to simulate a virtual bolus by the procedure described here, so resulting in measurement-independent time series of display data sets. Computational fluid dynamics (CFD) may also be used in the course of a simulation. One remarkable feature of this embodiment is that if a fixed velocity of the contrast agent bolus is assumed and path lengths are used, it is not necessary to simulate the precise shape of the bolus, but instead only to model it based on the window function and its application to the time parameter set which is descriptive of the arrival times of the contrast agent. This makes it possible, in the absence of time information, nevertheless to arrive quickly and with minimal effort at images showing the influx or outflow behavior of the contrast agent in the form of display data sets.

In addition to the method, the disclosure also relates to an image processing device for carrying out the method, including a first establishing unit for establishing the time parameter set, a second establishing unit for establishing the mask data sets, and a third establishing unit for establishing the display data sets. All explanations with regard to the method may be applied analogously to the image processing device, such that the advantages which have already been stated may also be obtained therewith. Corresponding units may be embodied by hardware and/or software. The image processing device may be embodied as part of an angiography device, (e.g., an angiography device with a C-arm).

A computer program is, for example, directly loadable into a storage device of an image processing device and includes program modules for carrying out the acts of a method described herein when the computer program is executed in the image processing device. The computer program may be stored on an electronically readable data storage medium, which therefore includes electronically readable control information stored thereon which includes at least one stated computer program and is designed such that, when the data storage medium is used in an image processing device, a method described herein is carried out. The data storage medium may be a non-transient data storage medium, in particular a CD-ROM.

BRIEF DESCRIPTION OF THE DRAWINGS

Further advantages and details of the present disclosure are revealed by the exemplary embodiments described below and with reference to the drawings, in which.

DETAILED DESCRIPTION

Figure 1:
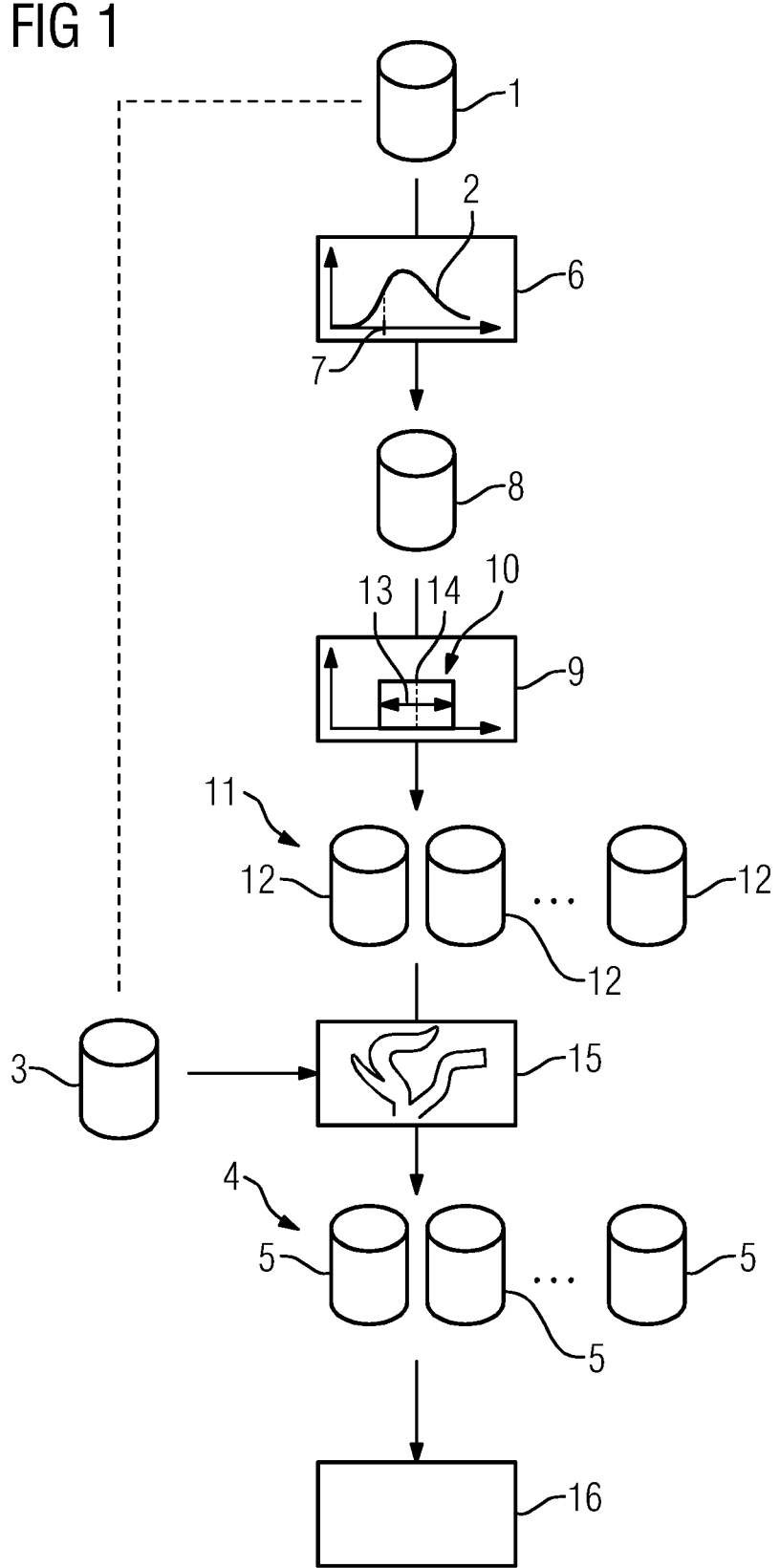
FIG. 1 depicts a sequence chart of an exemplary embodiment of the method.

FIG. 1 depicts a basic sequence chart of an exemplary embodiment of the method. The starting point therein is a four-dimensional (3D+t) angiography data set 1 from digital subtraction angiography. The angiography data set 1 includes, as is known in principle, a plurality of image data subsets, which in each case show different instants of a period in which a contrast agent bolus moves through the capture region of interest of a patient's vascular system covered by the angiography data set 1. In other words, for each voxel (e.g., picture element) represented in the image data subsets, a time profile 2 of contrast agent concentration in the voxel is established over the time interval by temporal concatenation of the corresponding image values which describe contrast agent concentration.

The problem associated with the angiography data set 1 is that an extremely extended contrast agent bolus was required for the production thereof, (e.g., a long injection time of for example 7 seconds), in order to obtain as many digital subtraction angiography projection images as possible in which at least large parts of the vascular system in the capture region are filled with contrast agent. Using these projection images as the basis, a high-quality three-dimensional vessel data set was produced which ultimately describes the limitations for the subsequent addition of the time information from the projection images over the entire time interval by multiplicative back-projection, when the angiography data set 1 is established. There are, of course, other conceivable possibilities for establishing the angiography data set in specific terms. The length of the contrast agent bolus, however, means that the arterial influx phase and the venous outflow phase may no longer be clearly separated and overlap, so complicating interpretation of the angiography data set 1 or of a succession of displayed image data subsets.

The exemplary embodiment of the method shown here now serves to produce a time series 4 of three-dimensional display data sets 5 which show the passage of a shorter, virtual contrast agent bolus through the vessel system in the capture region and may be interpreted as a new angiography data set. The arterial influx phases and venous outflow phases may be clearly differentiated in the time series 4, wherein it may also be stated that the time series 4 is a particularly capable display which requires little effort to establish of the bolus arrival time at various positions in the vascular system. The breakdown of the time series 4 may correspond to that of the time series of image data subsets of the angiography data set 1.

In act 6 of the method, the time profiles 2 for all the voxels of the capture region are analyzed in order to determine the arrival time 7 of the contrast agent bolus for each voxel. The time may be defined in various manners which are known in principle. In alternative exemplary embodiments, the instant of maximum contrast agent concentration may also be determined as the time parameter instead of the arrival time 7 of the contrast agent bolus (BAT).

The result of act 6 is a three-dimensional, static time parameter set 8, in which an arrival time 7 of the contrast agent bolus is assigned to each voxel in the capture region which is covered by the image data subsets.

In act 9, the window functions 10, shown by way of example in FIG. 1 as a rectangular function, for different windows which each correspond to different subintervals of the parameter space covered by the time parameters are applied to the time parameter set 8, such that a time series 11 of mask data sets 12 is obtained. All the window functions 10 used here have a constant window width 13, wherein the window per se, by displacing the center point thereof, is displaced through the entire time parameter space to produce the time series. The procedure is thus begun with windows which correspond to subintervals of early bolus arrival times 7, wherein for each instant the window and thus the subinterval is displaced towards later bolus arrival times 7 until the time parameter space has been passed through. Application of the window function 10 thus results in those arrival times 7 which are located within the subinterval defined by window being selected from time parameter set 8. The window width remains identical, wherein exemplary embodiments are conceivable in which the window width increases at later instants in order to display "blurring" of the contrast agent bolus.

In the case of the rectangular function shown as the window function 10 in FIG. 1, binary mask data sets 12 are ultimately obtained which contain the value "0" when the time parameter, in this case thus the arrival time 7, are located outside the subinterval defined by the window and "1" for arrival times 7 which are located within the subinterval defined by the window. By analogy with a virtual bolus, it may thus be stated that the bolus sharply defined here by the rectangular function has a length which corresponds to the window width 13, wherein the position of the bolus within the vascular system in the capture region is determined by the location of the center point 14 of the window. Because the location of the center point 14 is displaced towards higher time parameters by low time parameters, the virtual bolus is therefore also notionally pushed through the vascular system in the capture region, wherein the arrival times 7 known from the angiography data set 1 are taken into account.

Expressed in formulae, this means that, if the arrival time 7 is denoted BAT, the window function $f_\tau(BAT)$, $\tau$ describes an instant of the time series 4, 11 and $M_\tau(X)$ denotes the value of the mask data set at voxel x:

$$M_\tau(x) = f_\tau(BAT(x)).$$

Figure 2:
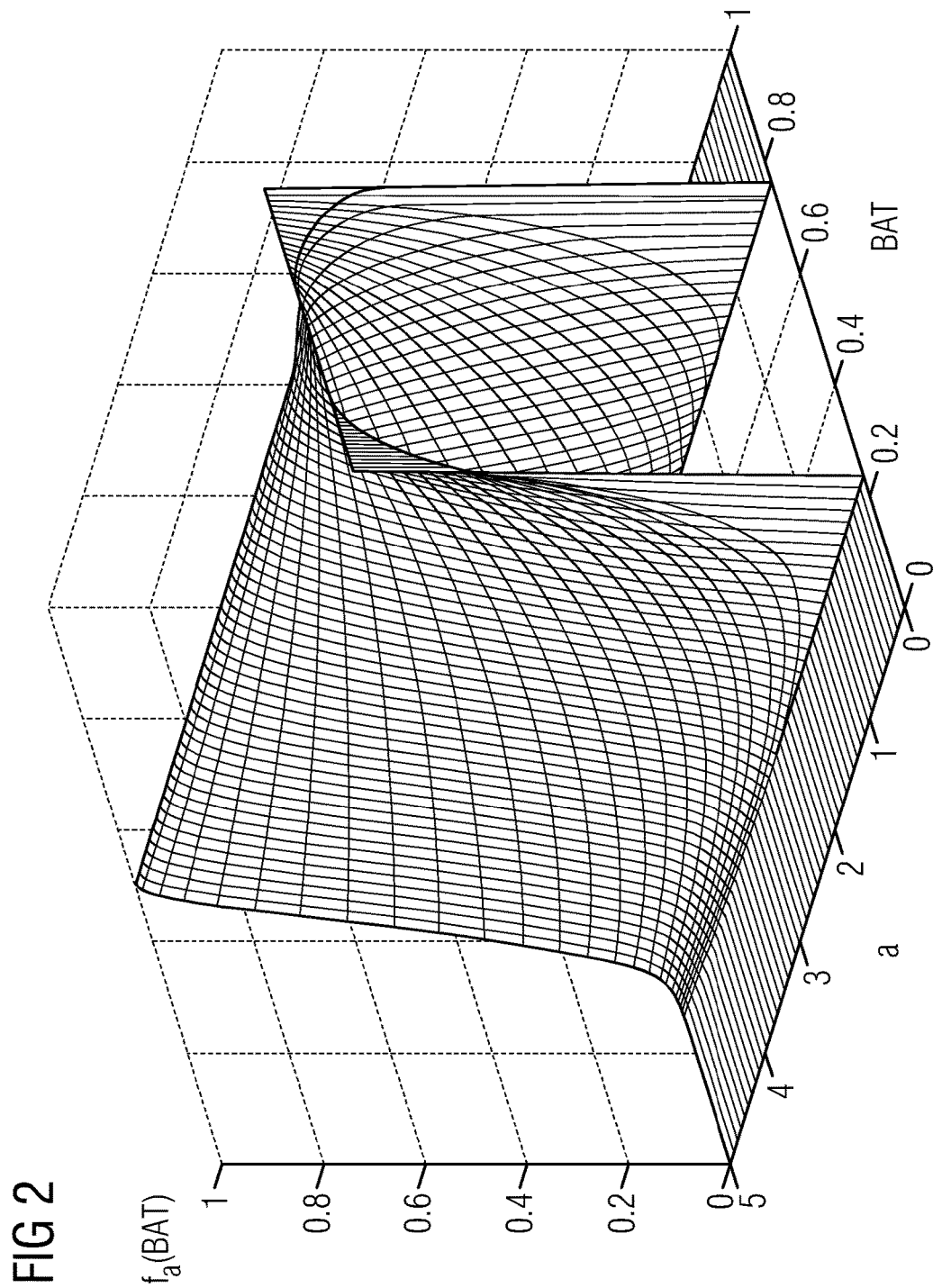
FIG. 2 depicts one possible development of the window function for a specific instant.

In order to be able to improve the display of a virtual bolus with a slowly rising contrast agent concentration and a slowly declining contrast agent concentration, the window function 10 may be a cosine-based window function, as shown by way of example in FIG. 2, instead of the rectangular function shown by way of example in FIG. 1. In the representation shown therein, a weighting value normalized to an interval from 0 to 1 is plotted as the result of the window function 10 in the mask data sets 12 on the one hand against arrival time 7 (BAT) for a fixed instant in the time series 4, 11, on the other hand against a shape parameter a which defines window width 13 and thus a length of the virtual bolus.

While the window width 13 of the cosine-based window function 10 of FIG. 2 corresponds to the length of the virtual contrast agent bolus, the center point 14 of the window (here the maximum) corresponds to an instant in the time series 4, 11 (and in particular, also to the time series of the image data subsets of the angiography data set 1), therefore to a flow phase of the contrast agent. While user selection of the center point 14 of the window corresponds to a selection of the display data set 5 which is to be displayed and is yet to be established, user adaptation of the shape parameter a, thus of window width 13, leads to an adaptation of bolus length, in which new display data sets 5 are determined and visually displayed in real time by the method described herein.

In order to establish the display data sets 5, the mask data sets 12 for the respective instant are produced in act 15 on the vessel data set 3, which provides a high-quality view of blood vessels of the vascular system in the capture region which are least temporarily filled with contrast agent. If binary mask data sets are obtained due to a window function 10 in the form of a rectangular function, applying a mask data set 12 to the vessel data set 3 means that the voxel contents of the vessel data set 3, for which the arrival time 7 of the contrast agent bolus was located in the corresponding subinterval, are displayed and the others not. However, also when values of between 0 and 1 may be assigned to voxels of the mask data sets 12, the mask data set 12 is applied voxel-by-voxel multiplicatively to the vessel data set 3, (e.g., the mask value of mask data sets 12), which now corresponds to a weighting value, determines how strongly the image content of the respective voxel of the vessel data set 3 is displayed.

Expressed in formulae, if an image value of the vessel data set 3 is denoted I(x), a display value with $D_\tau(x)$ is obtained as:

$$D_\tau(x) = I(x) \cdot M_\tau(x).$$

This proceeds correspondingly for all instants τ of the time series 4, 11.

In act 16, the display data sets 5 are displayed in a user interface on a visual display device. By the operating elements, (e.g., slider controls), an operator may select both the window width 13 and the instant and therefore vary the length of the virtual bolus and/or so to speak push the bolus through the vascular system in the capture region.

Figure 3:
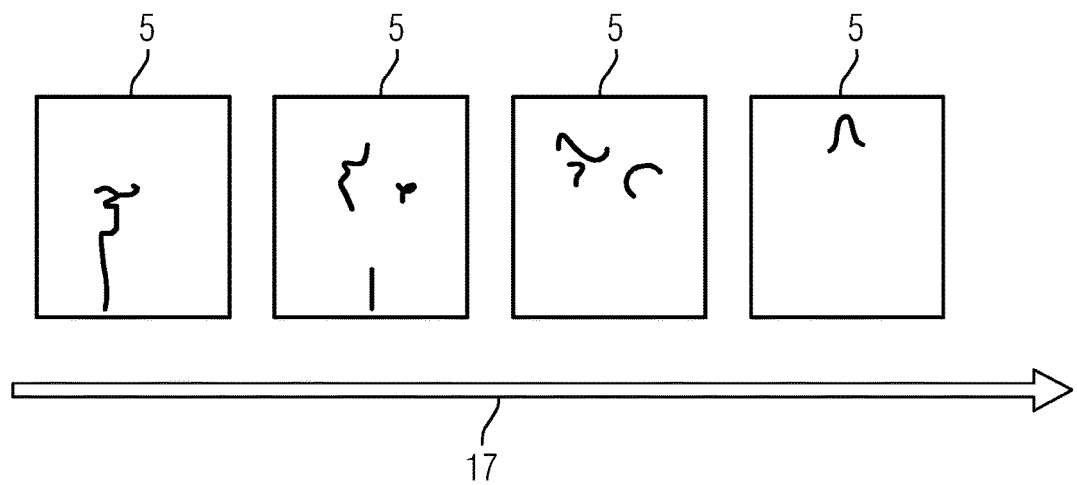
FIG. 3 depicts an example of a time series of display data sets.

FIG. 3 depicts a possible resultant display of display data sets 5. The arrow 17 here indicates the passage of time in the time interval, therefore the flow phase. As is apparent, the propagation of contrast agent in the capture region may be clearly inferred from the individual display data sets 5, which are assigned to different instants, wherein in particular the arterial influx phase and the venous outflow phase may be clearly differentiated.

It should additionally be noted that a virtual bolus need not necessarily be simulated with the method but, in particular instead of the arrival time 7 of the contrast agent in a voxel, it is also possible to display other time parameters, in particular also relative time parameters, in this manner.

Figure 4:
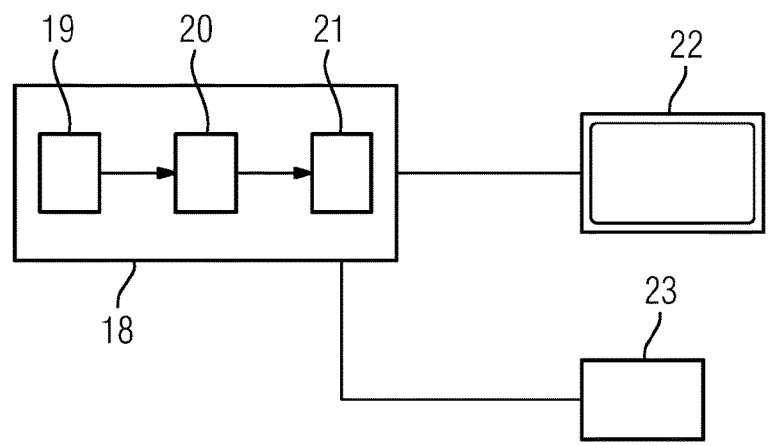
FIG. 4 depicts an example of an image processing device.

FIG. 4 depicts a rough schematic diagram of an image processing device 18, which in the present case may contain a first establishing unit 19 for establishing the time parameter set 8, a second establishing unit 20 for establishing the mask data sets 12 and a third establishing unit 21 for establishing the display data sets 5. A display unit, which is not shown in greater detail, may also be provided in order to display the display data sets 5 on a visual display device 22, wherein an input apparatus 23 may furthermore be present in order for example to select the display data set 5 to be displayed and/or to adapt shape parameters.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for image processing an angiography data set of a capture region of interest of a patient's vascular system, the angiography data set comprising a time series of two-dimensional or three-dimensional image data subsets of the capture region which, for spatial picture elements, describe a time profile of a contrast agent concentration of a contrast agent used during capture of the angiography data set, the method comprising:
   establishing a static time parameter set from the angiography data set, wherein the static time parameter set comprises time parameters and characterizes the time profile of the contrast agent concentration for picture elements of the capture region described in the image data subsets;
   establishing a series of mask data sets by picture element-by-picture element application of a window function having a window width of greater than zero;
   selecting a subinterval in a parameter space covered by the time parameters for each instant of the series of mask data sets to the static time parameter set; and
   establishing a series of static display data sets by applying the mask data sets to a static vessel data set, which shows a vascular system perfused by the contrast agent in the capture region and which underlies or is derived from the angiography data set.

2. The method of claim 1, wherein the static time parameter set contains absolute time parameters.

3. The method of claim 1, wherein the time parameters describing a contrast agent arrival time or an instant of maximum contrast agent concentration in the respective picture element are established.

4. The method of claim 3, further comprising:
   using the window function to display influx behavior, wherein the window function selects all the time parameters up to a specific time, or
   using the window function to display outflux behavior, wherein the window function deselects all time parameters up to a specific time.

5. The method of claim 4, further comprising:
   selectively visually displaying the display data sets on a visual display device by an operator by an operating element.

6. The method of claim 1, wherein the window width is adapted based on user input.

7. The method of claim 1, wherein time-ordered subintervals succeed one another in the time series.

8. The method of claim 1, wherein the window function is one or more of a rectangular function, a trapezoidal function, or a cosine-based function.

9. The method of claim 1, further comprising:
   selectively visually displaying the display data sets on a visual display device by an operator by an operating element.

10. The method of claim 9, wherein the window width is adapted based on user input.

11. The method of claim 9, wherein time-ordered subintervals succeed one another in the time series.

12. The method of claim 9, wherein the window function is one or more of a rectangular function, a trapezoidal function, or a cosine-based function.

13. An image processing device comprising:
- a first establishing unit configured to establish a static time parameter set from an angiography data set, wherein the angiography data set comprises a time series of two-dimensional or three-dimensional image data subsets of the capture region which, for spatial picture elements, describe a time profile of a contrast agent concentration of a contrast agent used during capture of the angiography data set, and wherein the static time parameter set comprises time parameters and characterizes the time profile of the contrast agent concentration for picture elements of the capture region described in the image data subsets;
- a second establishing unit configured to establish a series of mask data sets by picture element-by-picture element application of a window function having a window width of greater than zero; and
- a third establishing unit configured to establish a series of static display data sets by applying the mask data sets to a static vessel data set, which shows a vascular system perfused by the contrast agent in the capture region and which underlies or is derived from the angiography data set.

14. A computer program configured to be stored on an image processing device, wherein the computer program, when executed on the image processing device, is configured to cause the image processing device to at least perform:
- establish a static time parameter set from the angiography data set, wherein the angiography data set comprises a time series of two-dimensional or three-dimensional image data subsets of the capture region which, for spatial picture elements, describe a time profile of a contrast agent concentration of a contrast agent used during capture of the angiography data set, and wherein the static time parameter set comprises time parameters and characterizes the time profile of the contrast agent concentration for picture elements of the capture region described in the image data subsets,
- establish a series of mask data sets by picture element-by-picture element application of a window function having a window width of greater than zero;
- select a subinterval in the parameter space covered by the time parameters for each instant of the series to the static time parameter set; and
- establish a series of static display data sets by applying the mask data sets to a static vessel data set, which shows a vascular system perfused by the contrast agent in the capture region and which underlies or is derived from the angiography data set.

15. An electronically readable data storage medium on which a computer program is stored, wherein the computer program is configured to cause an image processing device to at least perform:
- establish a static time parameter set from the angiography data set, wherein the angiography data set comprises a time series of two-dimensional or three-dimensional image data subsets of the capture region which, for spatial picture elements, describe a time profile of a contrast agent concentration of a contrast agent used during capture of the angiography data set, and wherein the static time parameter set comprises time parameters and characterizes the time profile of the contrast agent concentration for picture elements of the capture region described in the image data subsets,
- establish a series of mask data sets by picture element-by-picture element application of a window function having a window width of greater than zero;
- select a subinterval in the parameter space covered by the time parameters for each instant of the series to the static time parameter set; and
- establish a series of static display data sets by applying the mask data sets to a static vessel data set, which shows a vascular system perfused by the contrast agent in the capture region and which underlies or is derived from the angiography data set.

* * * * *

UNITED STATES PATENT AND TRADEMARK OFFICE
CERTIFICATE OF CORRECTION

PATENT NO. : 10,223,820 B2
APPLICATION NO. : 15/874998
DATED : March 5, 2019
INVENTOR(S) : Markus Kowarschik et al.

It is certified that error appears in the above-identified patent and that said Letters Patent is hereby corrected as shown below:

In the Claims

"3. The method of claim 1, wherein the time parameters describing a contrast agent arrival time or an instant of maximum contrast agent concentration in the respective picture element are established."

Should be replaced with:
"3. The method of claim 1, wherein time parameters of the static time parameter set describing a contrast agent arrival time or an instant of maximum contrast agent concentration in the respective picture element are established."

"4. The method of claim 3, further comprising:
using the window function to display influx behavior, wherein the window function selects all the time parameters up to a specific time, or
using the window function to display outflux behavior, wherein the window function deselects all time parameters up to a specific time."

Should be replaced with:
"4. The method of claim 3, further comprising:
using the window function to display influx behavior, wherein the window function selects all time parameters of the static time parameter set up to a specific time, or
using the window function to display outflux behavior, wherein the window function deselects all time parameters of the static time parameter set up to a specific time."

Signed and Sealed this
Twenty-eighth Day of May, 2019

Andrei Iancu
*Director of the United States Patent and Trademark Office*

CERTIFICATE OF CORRECTION (continued)
U.S. Pat. No. 10,223,820 B2

"5. The method of claim 4, further comprising:
selectively visually displaying the display data sets on a
visual display device by an operator by an operating
element."

Should be replaced with:
"5. The method of claim 4, further comprising:
selectively visually displaying the static display data sets on a
visual display device by an operator by an operating
element."

"9. The method of claim 1, further comprising:
selectively visually displaying the display data sets on a
visual display device by an operator by an operating
element."

Should be replaced with:
"9. The method of claim 1, further comprising:
selectively visually displaying the static display data sets on a
visual display device by an operator by an operating
element."

"13. An image processing device comprising: a first establishing unit configured to establish a static time parameter set from an angiography data set, wherein the angiography data set comprises a time series of two-dimensional or three-dimensional image data subsets of the capture region which, for spatial picture elements, describe a time profile of a contrast agent concentration of a contrast agent used during capture of the angiography data set, and wherein the static time parameter set comprises time parameters and characterizes the time profile of the contrast agent concentration for picture elements of the capture region described in the image data subsets; a second establishing unit configured to establish a series of mask data sets by picture element-by-picture element application of a window function having a window width of greater than zero; and a third establishing unit configured to establish a series of static display data sets by applying the mask data sets to a static vessel data set, which shows a vascular system perfused by the contrast agent in the capture region and which underlies or is derived from the angiography data set."

Should be replaced with:
"13. An image processing device comprising: a first establishing unit configured to establish a static time parameter set from an angiography data set, wherein the angiography data set comprises a time series of two-dimensional or three-dimensional image data subsets of a capture region which, for spatial picture elements, describe a time profile of a contrast agent concentration of a contrast agent used during capture of the angiography data set, and wherein the static time parameter set comprises time parameters and characterizes the time profile of the contrast agent concentration for picture elements of the capture region described in the image data subsets; a second establishing unit configured to establish a series of mask data sets by picture element-by-picture element application of a window function having a window width of greater than zero; and a third establishing unit configured to establish a series of static display data sets by applying the mask data sets to a static vessel data set, which shows a vascular system perfused by the contrast agent in the capture region and which underlies or is derived from the angiography data set."

"14. A computer program configured to be stored on an image processing device, wherein the computer program, when executed on the image processing device, is configured to cause the image processing device to at least perform: establish a static time parameter set from the angiography data set, wherein the angiography data set comprises a time series of two-dimensional or three-dimensional image data subsets of the capture region which, for spatial picture elements, describe a time profile of a contrast agent concentration of a contrast agent used during capture of the angiography data set, and wherein the static time parameter set comprises time parameters and characterizes the time profile of the contrast agent concentration for picture elements of the capture region described in the image data subsets,
establish a series of mask data sets by picture element-by-picture element application of a window function having a window width of greater than zero; select a subinterval in the parameter space covered by the time parameters for each instant of the series to the static time parameter set; and establish a series of static display data sets by applying the mask data sets to a static vessel data set, which shows a vascular system perfused by the contrast agent in the capture region and which underlies or is derived from the angiography data set."

Should be replaced with:
"14. A computer program configured to be stored on an image processing device, wherein the computer program, when executed on the image processing device, is configured to cause the image processing device to at least perform: establish a static time parameter set from an angiography data set, wherein the angiography data set comprises a time series of two-dimensional or three-dimensional image data subsets of a capture region which, for spatial picture elements, describe a time profile of a contrast agent concentration of a contrast agent used during capture of the angiography data set, and wherein the static time parameter set comprises time parameters and characterizes the time profile of the contrast agent concentration for picture elements of the capture region described in the image data subsets, establish a series of mask data sets by picture element-by-picture element application of a window function having a window width of greater than zero; select a subinterval in a parameter space covered by the time parameters for each instant of the series of mask data sets to the static time parameter set; and establish a series of static display data sets by applying the mask data sets to a static vessel data set, which shows a vascular system perfused by the contrast agent in the capture region and which underlies or is derived from the angiography data set."

"15. An electronically readable data storage medium on which a computer program is stored, wherein the computer program is configured to cause an image processing device to at least perform: establish a static time parameter set from the angiography data set, wherein the angiography data set comprises a time series of two-dimensional or three-dimensional image data subsets of the capture region which, for spatial picture elements, describe a time profile of a contrast agent concentration of a contrast agent used during capture of the angiography data set, and wherein the static time parameter set comprises time parameters and characterizes the time profile of the contrast agent concentration for picture elements of the capture region described in the image data subsets, establish a series of mask data sets by picture element-by-picture element application of a window function having a window width of greater than zero; select a subinterval in the parameter space covered by the time parameters for each instant of the series to the static time parameter set; and establish a series of static display data

CERTIFICATE OF CORRECTION (continued)
U.S. Pat. No. 10,223,820 B2 sets by applying the mask data sets to a static vessel data set, which shows a vascular system perfused by the contrast agent in the capture region and which underlies or is derived from the angiography data set."

Should be replaced with:
"15. An electronically readable data storage medium on which a computer program is stored, wherein the computer program is configured to cause an image processing device to at least perform:
establish a static time parameter set from an angiography data set, wherein the angiography data set comprises a time series of two-dimensional or three-dimensional image data subsets of a capture region which, for spatial picture elements, describe a time profile of a contrast agent concentration of a contrast agent used during capture of the angiography data set, and wherein the static time parameter set comprises time parameters and characterizes the time profile of the contrast agent concentration for picture elements of the capture region described in the image data subsets, establish a series of mask data sets by picture element-by-picture element application of a window function having a window width of greater than zero; select a subinterval in a parameter space covered by the time parameters for each instant of the series of mask data sets to the static time parameter set; and establish a series of static display data sets by applying the mask data sets to a static vessel
data set, which shows a vascular system perfused by the contrast agent in the capture region and which underlies or is derived from the angiography data set."